US006328233B1

(12) United States Patent
Moy et al.

(10) Patent No.: US 6,328,233 B1
(45) Date of Patent: Dec. 11, 2001

(54) SPRAYER AND SYSTEM FOR CONTROLLED SPRAYING

(75) Inventors: Laurent Moy, Saint-Jean; Claude Accaries, Arudy, both of (FR)

(73) Assignee: Parfum Indigo, Gaillac (FR)

( * ) Notice: Subject to any disclaimer, the term of this patent is extended or adjusted under 35 U.S.C. 154(b) by 0 days.

(21) Appl. No.: 09/647,691

(22) PCT Filed: Apr. 2, 1999

(86) PCT No.: PCT/FR99/00779

§ 371 Date: Oct. 3, 2000

§ 102(e) Date: Oct. 3, 2000

(87) PCT Pub. No.: WO99/51358

PCT Pub. Date: Oct. 14, 1999

(30) Foreign Application Priority Data

Apr. 3, 1998 (FR) .................................................. 98 04156

(51) Int. Cl.[7] ............................. B05B 1/00; A62C 13/62; A62C 13/66; A62C 35/58; A61M 11/06

(52) U.S. Cl. ........................... 239/600; 239/302; 239/338

(58) Field of Search .................................... 239/302, 337, 239/338, 343, 369, 370, 311, 590.3, 590.5, 590, 600

(56) References Cited

U.S. PATENT DOCUMENTS 2,382,681 8/1945 Trier .
4,039,639 * 8/1977 Kankel et al. ................... 261/121 R
4,566,451 * 1/1986 Badewien ........................ 128/200.21
5,490,630 * 2/1996 Hecker ................................ 239/309
5,549,102 * 8/1996 Lintl et al. ...................... 128/200.21
5,570,840 * 11/1996 Gettinger et al. .................... 239/112
5,849,005 * 12/1998 Garrison et al. ......................... 606/1

FOREIGN PATENT DOCUMENTS 30 00 223 7/1980 (DE) .
0 608 176 8/1994 (EP) .

* cited by examiner

*Primary Examiner*—Kevin Shaver
*Assistant Examiner*—Davis Hwu
(74) *Attorney, Agent, or Firm*—Young & Thompson

(57) ABSTRACT

An apparatus for spraying a liquid into the atmosphere includes a container (1) for containing the liquid (2), having at least one outlet (3) for the liquid to be expelled outside the container, the outlet being located above the liquid, a device generating (4) a gas stream for expelling the liquid outside the container, a vaporizer (5) that vaporizes the liquid in the gas stream, a sprayer (6) that sprays the vaporized liquid and that includes a column with baffles located downstream of the vaporizer, the vaporizer and the sprayer being integral with a body (7) that is removably mounted on the container.

16 Claims, 3 Drawing Sheets

SPRAYER AND SYSTEM FOR CONTROLLED SPRAYING

BACKGROUND OF THE INVENTION

The present invention relates to apparatuses which permit a liquid to be sprayed into the atmosphere, comprising a container, which is intended to contain the liquid and has at least one outlet for the liquid to be expelled from the container, the outlet being situated above the liquid, means for generating a gaseous stream to expel the liquid from the container, means for vaporising the liquid in the gaseous stream, and means for spraying the vaporised liquid. Hereinafter, vaporisation is understood to mean the transformation of a liquid into fine droplets and the possible change thereof into the gaseous state, and spraying is understood to mean the transformation of the fine droplets obtained by vaporisation into very fine droplets.

Such apparatuses may be used as a simple product diffuser, or they permit scents to be diffused into the atmosphere when the liquid contained in the container is a fragrant liquid, in any place, depending on the wish or the needs of the user, more especially in the laboratory, to study the effect of the scent on the behaviour of individuals or the composition of the scents, in marketing agencies in order to ensure the promotion of a product, in supermarkets in order to influence the consumption of products, in any place to ensure that the place smells sweetly, etc. Uses of this type of apparatus in aromatherapy can also be envisaged.

Prior art discloses, more especially with the document EP 0 608 176, a spray of the type described above. The spray comprises a container containing the liquid to be sprayed, to the base of which is secured an inlet tube for the gaseous stream. The tube traverses the liquid in the container and is provided with a venturi at its upper end above the liquid, a venturi to which is laterally connected a suction duct for the liquid. The upper part of the container is extended by a distillation chamber, intended to reduce the dimension of the liquid droplets in suspension in the gaseous stream downstream of the venturi, and this is in order to diffuse a mist of very fine droplets at the spray outlet.

Such a spray operates well, but it has disadvantages which can greatly limit the possibilities of use thereof. In effect, the liquid is contained in a container which forms a body with the spray and at the base of which the venturi is secured, and this does not confer great flexibility of use. Such a configuration, moreover, leads to difficulty in cleaning the parts which make up the spray, particularly the container, more especially when it is desirable to use a different product, and a high cost of manufacture. Also, it is not easy to refill the container with spray product each time it is empty.

With the document EP 0 655 282, an apparatus is also known for spraying fragrant liquid, in which the liquid to be sprayed is situated in an exchangeable cartridge, which is disposable when it is empty. Here, it is the exchangeable cartridge which contains the venturi intended to vaporise the liquid. This type of spray may permit the disadvantages of the difficult refilling and cleaning of the spray previously described to be overcome. However it remains very onerous in use, since the cartridge, which is changed on every product refill, contains elaborate technical devices, more especially the venturi. In addition, since this cartridge is intended for single use, the spraying means which it contains cannot be as effective as those of an apparatus for which they are intended to be worn out over the lifetime of the apparatus.

SUMMARY OF THE INVENTION

The present invention proposes to overcome these disadvantages, and to provide other advantages. More precisely, it comprises an apparatus which permits a liquid to be sprayed into the atmosphere, comprising:

a container, which is intended to contain said liquid and has at least one outlet for the liquid to be expelled from said container, said outlet being situated above said liquid, means for generating a gaseous stream to expel said liquid from said container, means for vaporising said liquid in said gaseous stream, and means for spraying the vaporised liquid, comprising a column which is provided with baffles and is situated downstream of the vaporising means, characterised in that said vaporising means and said spraying means are integral with a body capable of being engaged and maintained in a detachable manner in said outlet of the container, said body including a duct for expelling the liquid from the container.

The apparatus according to the invention permits a simple container to be used to contain the liquid to be sprayed, said container being provided with an outlet which advantageously serves both for refilling and for expelling the liquid. Such a container may be of the bottle type, in the upper outlet of which will be situated the body containing, more especially, the spraying and vaporising means. Thus, the container will advantageously be able to be discarded when it is empty, with minimum production and operating costs, since this container will be able to be formed from the only means necessary to retain liquid inside, namely an air-tight envelope. Moreover, the apparatus according to the invention provides great flexibility and ease of use by this design. The vaporising and spraying means, re-used on each change of bottle, permit these means to be appropriately sophisticated, if necessary. The column provided with baffles permits the liquid to be sprayed to be micro-diffused, by virtue of the extreme fineness of the droplets obtained, which is necessary to permit a good suspension of the liquid sprayed into the atmosphere, low liquid consumption and better results in the matter of scent diffusion in the atmosphere, for example.

According to an advantageous characteristic, the vaporising means comprise a venturi.

According to another advantageous characteristic, the column comprises a plurality of inclined walls which form baffles on which said vaporised liquid comes to lodge, and the inclined walls form an angle, greater than 90°, with the longitudinal flow direction of the stream, so as to avoid a reverse flow of said stream.

According to another advantageous characteristic, said inclined walls each include a hole for the passage of the stream, the respective holes of two successive walls being offset.

According to another advantageous characteristic, said hole assumes the form of a venturi.

According to another advantageous characteristic, two successive inclined walls are symmetrical relative to a plane which is perpendicular to the longitudinal flow direction of the stream.

According to another advantageous characteristic, the means for generating a gaseous stream to expel the liquid from the container comprise a flow accelerator situated downstream of the spraying means.

According to another advantageous characteristic, the flow accelerator comprises a fluid flow, which envelops said gaseous stream and the sprayed liquid downstream of the spraying means.

According to an alternative to the preceding characteristic, said flow accelerator comprises a fluid flow conveyed in an axial manner into a venturi-type duct, which includes a tapering part followed by a cylindrical part, said gaseous stream and the sprayed liquid being introduced laterally into said cylindrical part of said venturi-type duct.

The invention also relates to a system which permits the spraying of a liquid into the atmosphere to be controlled, characterised in that it comprises at least:

one apparatus, which permits a liquid to be sprayed into the atmosphere according to the invention, one gas sensor, which permits measurement of the concentration of the liquid sprayed into the atmosphere, and means for controlling the operation of said apparatus in dependence on at least one predetermined input command and on said measurement provided by said gas sensor.

BRIEF DESCRIPTION OF THE DRAWINGS

Other characteristics and advantages will become apparent on reading the following description of an example of an embodiment of an apparatus and a system according to the invention, together with the accompanying drawings, such an example being given by way of illustration and without any restrictive interpretation of the invention being able to be derived therefrom.

DESCRIPTION OF THE PREFERRED EMBODIMENTS

Figure 1:
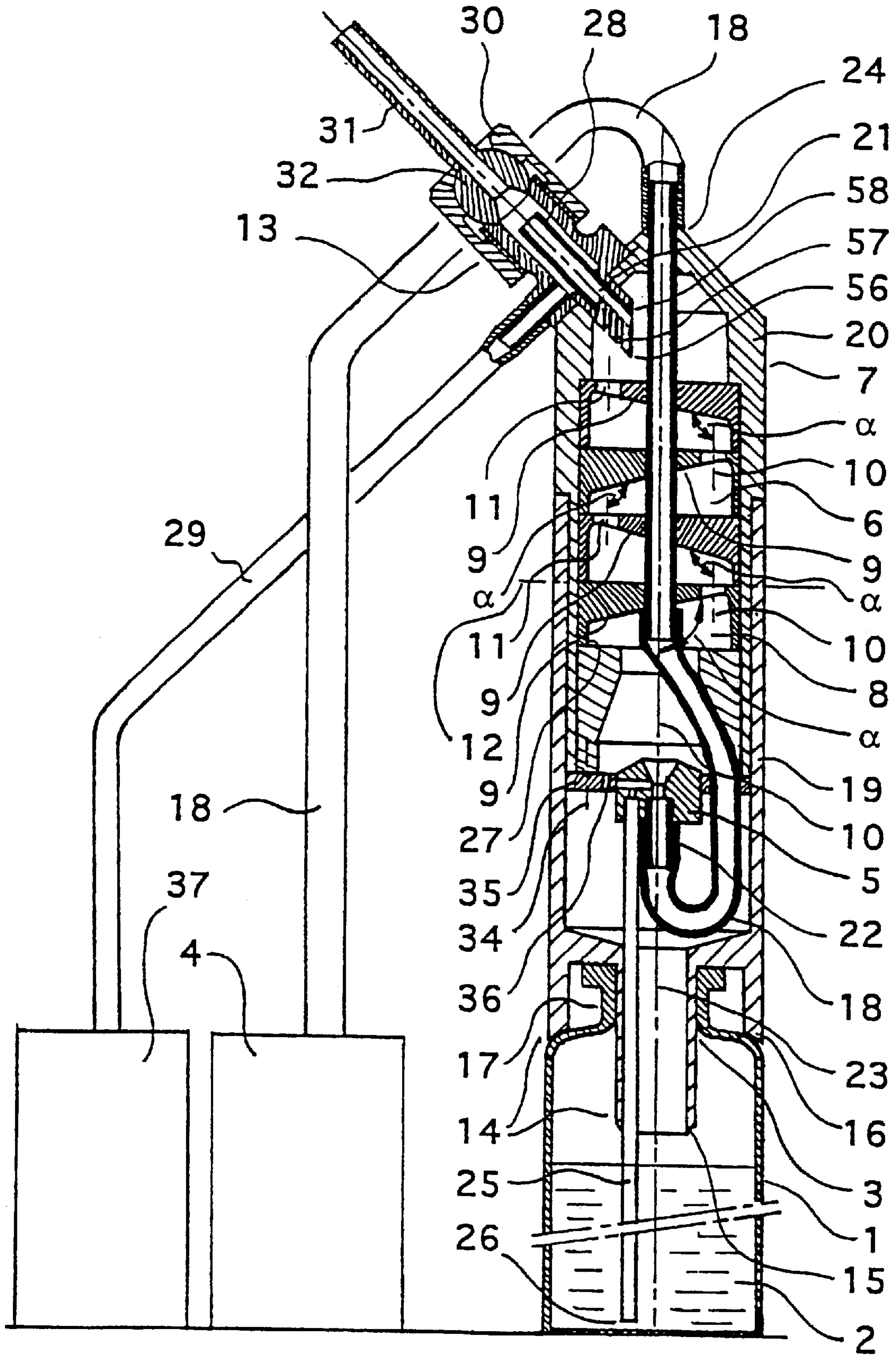
FIG. 1 is a longitudinal sectional view of a first example of an embodiment of an apparatus which permits a liquid to be sprayed into the atmosphere, according to the invention.

In FIG. 1, the apparatus which permits a liquid to be sprayed into the atmosphere, or spray, comprises a container 1, intended to contain the liquid 2 to be sprayed, the container 1 having an outlet 3 for expelling the liquid from the container, the outlet 3 being situated above the liquid 2, means 4 for generating a gaseous stream to expel the liquid 2 from the container 1, means 5 for vaporising the liquid 2 in the gaseous stream, and means 6 for spraying the vaporised liquid.

The vaporising means 5 and the spraying means 6 are integral with a body 7 capable of being engaged and maintained in a detachable manner in the outlet 3 of the container 1, as illustrated in FIG. 1, the body 7 containing a duct 8 for expelling the liquid 2 from the container 1.

The container may advantageously be formed by a bottle 1 for packaging the product to be sprayed. For this purpose, the single outlet 3 of the bottle 1 serves for refilling and expelling the liquid 2, and will contain an air-tight stopper (not illustrated), used for packaging the product, this stopper being removed to engage the body 7 in the outlet. The bottle 1 will advantageously be rigid or semi-rigid, so as to permit the body 7 to be maintained in the engaged position in the outlet 3. For this purpose, the body 7 will have, at one of the ends thereof, a form 14, which is capable of coming into engagement on the upper part of the bottle 1 comprising the outlet 3. For example, the form 14 will be able to include, as illustrated in FIG. 1, a tube 15, maintaining contact in the outlet 3 or on the flange 17 of the bottle by force-fitting or by a helically threaded assembly (not illustrated) or the like and, if necessary, an additional abutment 16, resting on the upper part of the bottle 1 or of the flange 17 thereof. The form 14 of the body 7 will obviously be adapted to that of the container 1 which is used, with a view to assembling these two elements. The container 1 or the body 7 will contain any venting means which permits the liquid in the body to be emptied from the container by suction, as described hereinafter.

The body 7 will be hollow in order to accommodate the vaporising and spraying means, as explained later, and will have to permit, on the one hand, the liquid 2 to be sucked up via its lower part through the outlet 3 of the bottle 1 and, on the other hand, to permit the gaseous stream containing the sprayed liquid to emerge via its upper part. The body 7 will be formed from a rigid material, for example steel or plastics material, and will advantageously be made up of two parts 19 and 20, which are detachable from each other in order to facilitate access to the interior of the body 7. In the example of FIG. 1, the body 7 assumes the form of a tube in two parts, a lower part 19 containing, at the lower end thereof, the form 14 already described to connect with a container, and an upper part 20, for example threaded (not illustrated) or force-fitted onto the lower part 19, which contains, at the upper end thereof, an opening 21 through which the liquid sprayed in the gaseous stream emerges.

The means for generating a gaseous stream to expel the liquid 2 from the bottle 1 comprise a pump 4, which delivers a discharge of gas conveyed towards the body 7 by means of a conduit 18, as will be explained later with a description of the vaporising means. The gas used will depend on the use of the spray, and will advantageously be the ambient air in the case of scent diffusion from a fragrant liquid 2, as illustrated in the example.

The means for vaporising the liquid 2 in the gaseous stream advantageously comprise a venturi 5 situated, for example, in the longitudinal axis 23 of the body 7, in the lower part thereof, but advantageously secured to the upper part 20 by means of a plate 35 and screws 34, for example, in order to form an upper body part 7 which is compact and contains the means for vaporising and spraying the liquid. Thus, the lower part 19 of the body has the simple function of supporting the form 14 which permits the body 7 to be connected to the container 1. In the event of a change in the shape of the container 1, only the lower detachable part 19 of the body 7 will have to be replaced.

The plate 35 for securing the venturi 5 will advantageously contain at least one through-passage 36, which permits the liquid, which has been insufficiently vaporised and which would not be drawn into the spraying means 6 because the weight of the droplets is too great, to return downwardly by gravity, upstream of the spraying means, into the container 1 through the outlet 3. The passage 36 may, for example, be formed from at least one hole situated in the low part of the plate 35.

The conduit 18 conveys the air stream into the body 7 as far as the lower end 22 of the venturi 5, by passing through the upper end 24 of the body 7 along the longitudinal axis 23 of this body into the upper part 20, which contains the spraying means situationed above the vaporising means, then continuing, in an offset manner, into the lower part 19 of the body 7, in order that the conduit 18 may be replaced in the longitudinal axis 23 of the body 7, while directing the air stream towards the upper end 24 of the body 7, as illustrated in FIG. 1. It is to be noted that the conduit 18 could penetrate into the body 7 and follow a path of a different manner to that previously described. The function of the conduit 18 is, in fact, to convey the air stream to the inlet of the venturi 5, in order to create a low pressure on the internal wall of this venturi on which terminates a duct 25, the other end 26 of which is immersed in the liquid 2, as illustrated in FIG. 1. The liquid 2 is thereby sucked into the venturi 5 and vaporised in the air stream upwardly in the direction of the spraying means. A lateral inlet of the conduit 18 into the body 7 may be effected, for example, in an alternative manner, for example in the lower part 19 thereof (not illustrated).

The spraying means comprise a column 6 with baffles, situated downstream of the venturi 5, to spray the vaporised liquid 2, i.e. above the venturi 5, depending on the layout, along a vertical axis of the means illustrated in FIG. 1. The venturi 5 permits the liquid 2 to be vaporised into fine droplets in the air stream, and the column 6 with the baffles permits these fine droplets to be split into particles of a size in the order of a few micrometers, suitable for better diffusion of the liquid in the atmosphere into which it is expelled through the outlet 21 of the body 7 downstream of the column 6. For this, the column 6 advantageously comprises a plurality of inclined walls 9, situated substantially one above the other and forming baffles on which the diphasic flow comes to lodge, moving generally from bottom to top, i.e. the liquid vaporised in the gaseous stream, the inclined walls 9 forming an angle α, greater than 90°, with the longitudinal direction 10 of the flow, so as to prevent a reverse flow of this liquid between the impact zone of the diphasic flow on a wall and the hole through which this liquid passes to the following wall. The angle α will preferably be between 95° and 135°, for example substantially equal to 105°, as in the example illustrated in FIG. 1. The value of the angle α is dependent on the size of the particles which it is desirable to obtain at the outlet of the spray; the nearer the angle α is to 90°, the finer are the particles of sprayed liquid, and the further it is from 90°, the more the flow of the stream is improved and the larger are the particles. The movement from bottom to top of the liquid vaporised in the gaseous stream, then that of the diphasic flow in the column with baffles, permits gravity to be used to prevent the liquid droplets, which are not sufficiently fine relative to the use for which the spray apparatus according to the invention is intended, from being drawn towards the outlet at any point and, on the contrary, to direct these droplets in the direction of the liquid container where they may thus follow, once again, the full circuit of vaporising and spraying, or a partial circuit of spraying in the case of partial return into the spraying means.

Each wall 9 may, for example, be supported by a tubular connection 27, which has an external configuration complementary to the internal configuration of the upper part 20 of the body 7, thereby permitting the external surface of the tubular connection 27 to be fitted edge-to-edge on the internal surface of the upper part 20 of the body 7 and the walls 9 to be stacked in a useful manner, as illustrated in FIG. 1. A plurality of walls 9, thus provided with their own tubular connection, for example 4 walls, may be stacked one on top of the other in order to produce the column with baffles 6, the wall 9 and its tubular connection 27 being inscribed in an upright cylinder in the example illustrated.

Each inclined wall 9 will advantageously contain a hole 11 for the diphasic flow to pass therethrough, the respective holes 11 of two successive walls 9 being offset, so as to ensure an impact of the flow on the following wall without directly traversing the hole 11. The hole 11, for example, will be cylindrical, of circular or oblong cross-section, and will be situated on the wall substantially in the zone most downstream from the impact of the flow on this wall, in the longitudinal flow direction 10, as illustrated in FIG. 1. The wall of the hole 11 will preferably be non-tangential to the internal wall of the tubular connection 27 and will be slightly recessed towards the longitudinal axis 23 of the body 7, as illustrated in FIG. 1.

The holes of two successive walls 9 will be able to be symmetrically opposed relative to the longitudinal axis 23 of the body 7, and diametrically opposed in the case of a body of circular cross-section. The holes 11 will alternatively be able to be disposed so that the diphasic flow in the column 6 through the holes 11 assumes a general profile which is substantially helical, the holes being angularly offset in the same direction of rotation according to a predetermined step, for example regular.

In the configuration of two successive holes 11, symmetrically opposed relative to the longitudinal axis 23 of the body 7, two successive inclined walls 9 will be able to be symmetrical relative to a plane 12 perpendicular to the longitudinal direction 10 of the flow, as illustrated in FIG. 1, this being in order to permit the diphasic flow to be regular.

Figure 2:
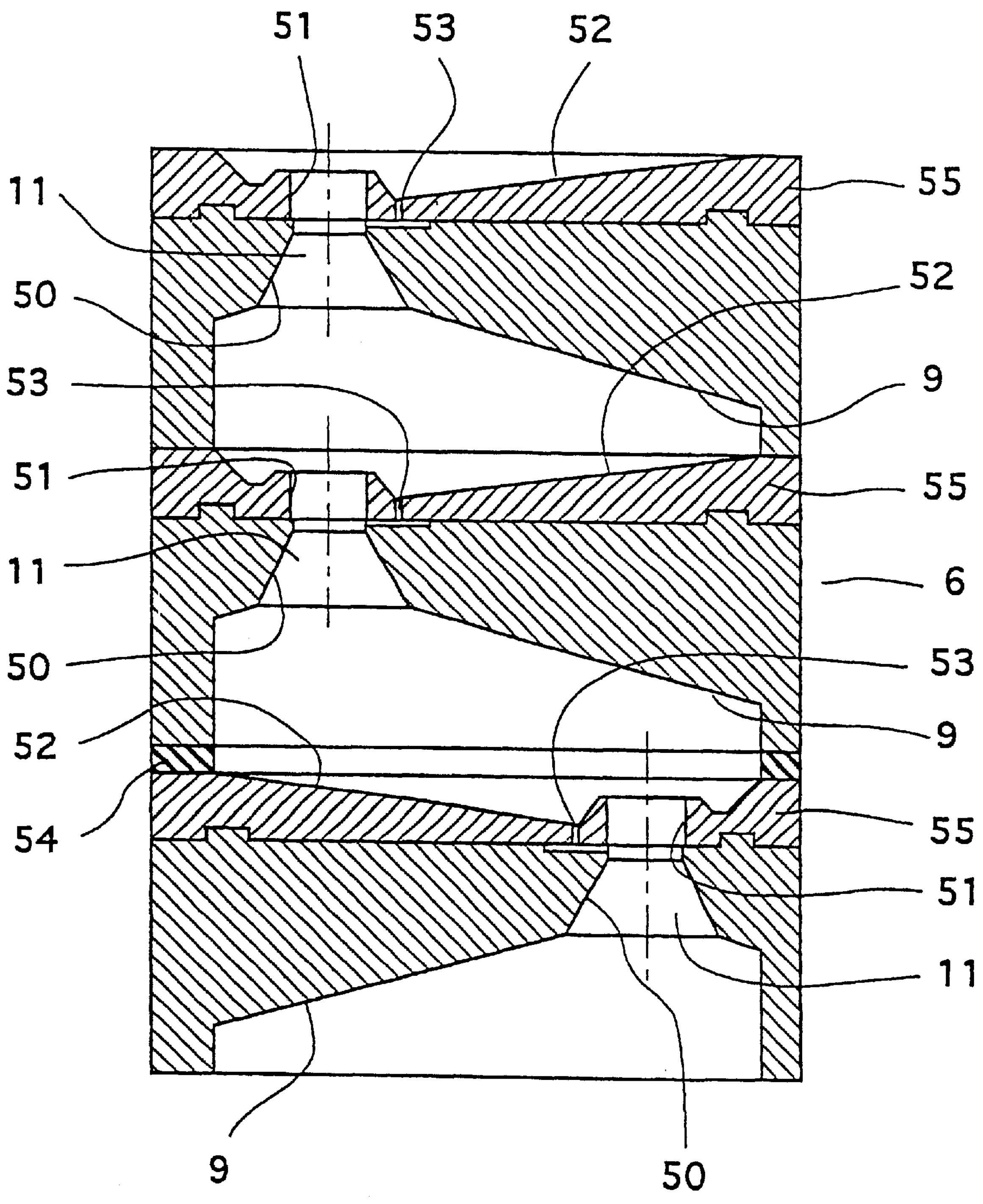
FIG. 2 is a longitudinal sectional view of a second example of an embodiment of an enlarged detail of the apparatus in FIG. 1.

Advantageously, as illustrated in FIG. 2, the holes 11 for the flow to pass from one wall 9 to the following wall will assume a venturi-type structure containing a tapering part 50 followed by a cylindrical part 51. It is to be noted that, in FIG. 2, the elements fulfilling a function similar to that of elements in FIG. 1, bear the same reference numeral. The venturi-type hole 11 here permits the output of the spray column to be increased and contributes towards optimising the splitting of the particles to increase the homogeneity factor of the particles for a given particle size. Starting from the second wall in the direction of flow after the venturi 5, the column 6 advantageously comprises, below each wall 9, a funnel 52 which permits the liquid not drawn into the diphasic flow to be collected by gravity, and to convey it into the venturi-type hole 11 according to two alternatives, which are described below.

The first alternative (not illustrated) consists in the lowest part of a funnel 52 being connected to the outlet of the hole 11 situated upstream, so that the liquid drained by the funnel 52 flows by gravity into the hole 11 and is thereby returned to the diphasic flow at the outlet of the hole. A second alternative consists in the outlet of the hole 11, situated upstream, rising above the low part of the funnel 52, and a duct 53 being provided in the base of the funnel 52 conveying the condensed liquid into the hole 11 and, more particularly, into the cylindrical part of the hole 11, as illustrated in FIG. 2. This second alternative is particularly effective for viscous liquids, since it permits the liquid to be reliably vaporised in the hole 11 by the venturi effect. The funnels and ducts 53 permit the baffles to avoid becoming clogged by an accumulation of product, should the occasion arise.

The spray column illustrated in FIG. 2 advantageously comprises wedges 54 of a thickness which permits the distance separating the outlet of a hole 11 from the following wall 9 to be adjusted, and this is with the aim of ensuring that the granulometry of the liquid particles is regulated. Generally, the distance between the venturi 5 and the first wall 9, and the distances between the outlet of a hole 11 and the following wall, will preferably decrease in the direction of the flow, and this is in order to help to optimise the reaction for splitting the liquid droplets. Jointly with the decrease in the distances defined above, the diameters of the holes 11 for the passage of the flow will preferably also be decreasing from the hole 11 of the first wall 9 to the hole of the last wall in the direction of flow.

As illustrated in FIG. 2, and in order to facilitate the manufacture of the ducts 53, the column 6 may comprise an element 55, interposed respectively between two successive walls 9 and supporting the funnel 52. One element 55 will advantageously be situated above the last wall 9 in the direction of flow.

The spray column illustrated in FIG. 2 could be inserted into the body 7 of the apparatus illustrated in FIG. 1, for example. It is to be noted that the passage for the supply conduit 18 of the gaseous stream to the venturi has not been illustrated in FIG. 2. Moreover, it is to be noted that the two successive holes 11 have been aligned in order to reduce the effects of the spray column, according to requirements.

The gaseous stream, containing the liquid 2 sprayed at the outlet from the last wall 9 of the column 6, is then expelled from the spray through the opening 21 at the top of the body 7. The opening 21 may be provided with a simple nozzle 28 if need be, fixed or directional depending on requirements.

The apparatus illustrated in FIG. 1 comprises means 4 for generating a gaseous stream to expel the liquid 2 from the container 1 as described above, which means additionally and advantageously contain a flow accelerator 13, situated downstream of the spraying means 6 and, more particularly, downstream of the opening 21 of the body 7, as illustrated in FIG. 1. The flow accelerator 13 preferably comprises a fluid flow which envelops the gaseous stream and the sprayed liquid, emerging from the nozzle 28.

The accelerator has the function of preventing or limiting the condensation of the liquid in the spray column, and this is done by creating a fluid flow which draws the gaseous stream and the sprayed liquid emerging from the body 7. Another function of the accelerating flow is to provide additional energy to the spayed liquid so as to project it to a greater and variable distance according to the supply of fluid flow which is drawn. Another function of the accelerating flow is to provide an insect trap by the projection of pheromone. Another function of the accelerating flow is to permit the sprayed liquid to be diluted.

In the example illustrated in FIG. 1, the emergence of the diphasic flow from the body 7 is aided by the friction of the fluid accelerating flow which envelops the diphasic flow. The fluid accelerating flow will be able to be provided by the pump 4, which generates the gaseous stream at the input of the venturi, and conveyed, on emerging from the body 7, by an auxiliary conduit tapped from the conduit 18 which supplies the venturi 5 with an air stream. The tapping may be effected at any point, preferably before the conduit 18 enters the body 7. Alternatively, and preferably, the accelerating flow will be provided by an independent pump 37 and conveyed to the body outlet by a conduit 29 which is independent of the conduit 18 for supplying the venturi. Thus, the accelerating flow will advantageously be able to be controlled and monitored independently of the gaseous flow supplying the venturi, with a view to obtaining greater flexibility of use and optimum adjustment of the accelerating flow relative to the diphasic flow for better performance of the spray.

The supply conduit for the fluid accelerating flow is connected to a nozzle 30 fitted, for example, on the nozzle 28, as illustrated in FIG. 1. The accelerating flow is provided around the nozzle 28 internally of the nozzle 30, so that it envelops the gaseous stream and the sprayed liquid, emerging from the nozzle 28, and this is in order to create maximum friction of the accelerating flow on the diphasic flow.

Additionally, the nozzle 30 may be provided with an outlet adjuster 31 for the accelerating flow, the gaseous stream and the sprayed liquid, the adjuster 31 being able to be mounted on a ball-and-socket joint 32 in order to permit the direction of output of the flow to be selected.

As illustrated in FIG. 1, the nozzle 28 penetrates inside the body through a projection 56, intended to avoid liquid droplets escaping through the opening 21. The projection 56 will be provided, on the external surface thereof, with at least one spout 57 to channel the liquid droplets which would be condensed on the projection, and in order to avoid these droplets being sucked into the flow emerging from the spray. For this purpose, the end face 58 of the projection 56 will preferably be vertical, the spout being made up of at least one groove situated in a vertical plane and surrounding the projection, as illustrated in FIG. 1.

Alternatively, the flow accelerator may be produced by using a venturi-type opening 21 (not illustrated), which contains a tapering part followed by a cylindrical duct part. In this case, the diphasic flow emerging from the spray column is introduced laterally, and in a regularly distributed manner, through lateral ducts, inside the cylindrical part of the upper opening of the venturi-type body, the accelerating flow being conveyed in an axial manner into the main duct of the venturi-type opening, that is to say into the tapering part. Thus, the diphasic flow penetrates into the outlet opening of the spray by the combined effects of the suction due to the venturi and the pressure due to the spray column, and it is accelerated towards the outlet of the spray.

Figure 3:
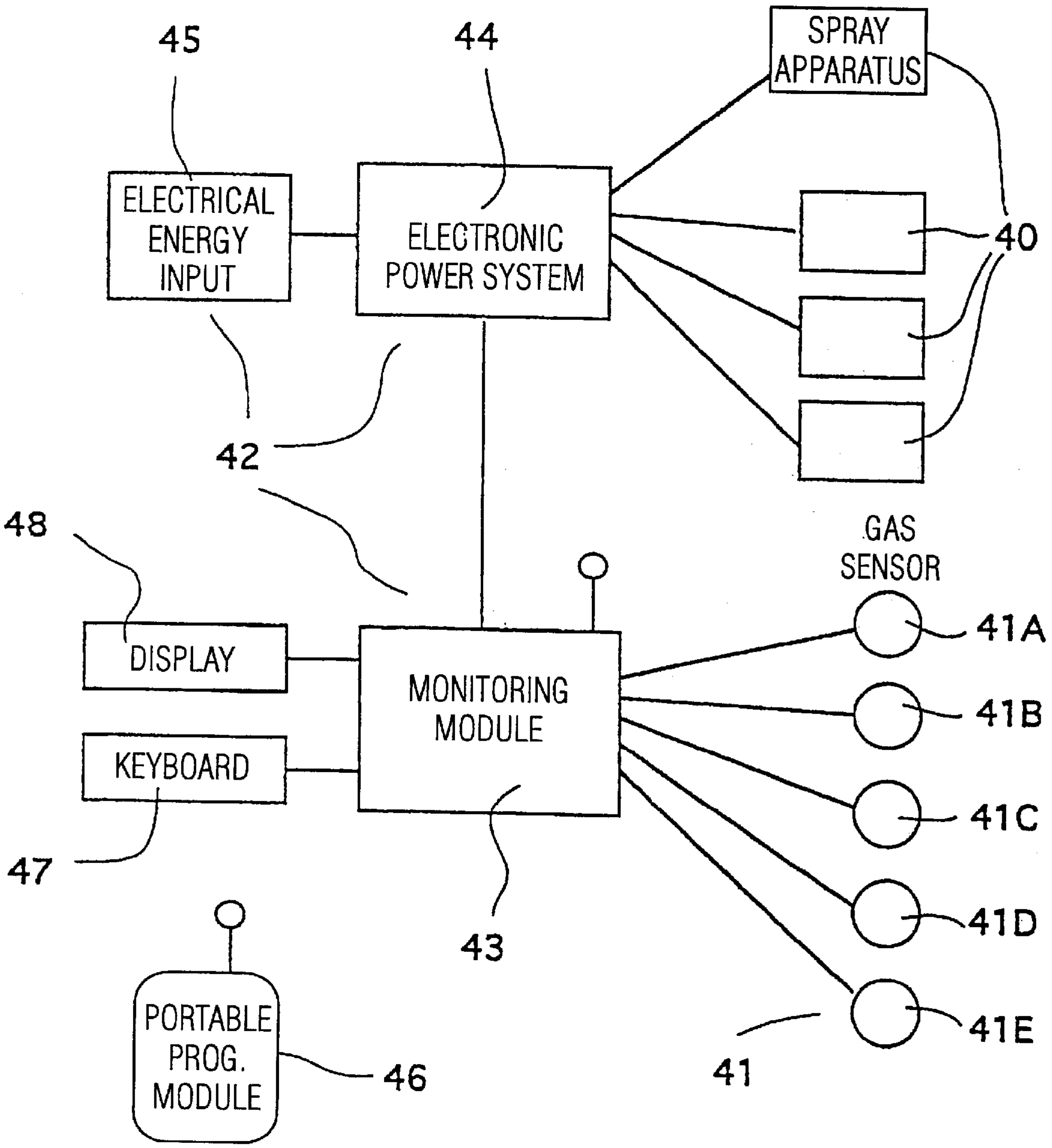
FIG. 3 is a perspective view of the whole of a system which permits the spraying of a liquid into the atmosphere to be controlled.

The system illustrated in FIG. 3, which permits the spraying of a liquid into the atmosphere to be monitored, comprises at least a plurality of apparatuses 40 according to the invention, as described previously for example, which permit a liquid to be sprayed into the atmosphere, a plurality of gas sensors 41A, which permit measurement of the concentration of the liquid sprayed into the atmosphere, and means 42 for controlling the operation of the apparatuses 40 in dependence on at least one predetermined input command and measurements provided by the gas sensors.

The control means 42 advantageously comprise an electronic module 43 for controlling and monitoring the apparatuses 40, an electronic power system 44 and an electrical energy input 45. The electronic controlling and monitoring module 43 is advantageously provided with permanent software for the emissions of sprayed liquid. The operator enters the input command or commands, by means of a keyboard 47, into the controlling and monitoring module 43, which transmits this input command or these input commands to the electronic power system 44 which controls the operation of the apparatuses 40 relative to this input command or these input commands, with the help of the sensors 41, more especially the gas sensors 41A which send back to the electronic module 43 measurements of the concentration of the liquid sprayed into the atmosphere. Thus, the above-described system according to the invention can operate automatically. The controlling and monitoring electronics will advantageously be provided with a display 48 for monitoring the operation of the system, on which will be able to appear the input commands as well as the values from the sensors 41.

The system according to the invention will advantageously be provided with a portable programming module 46, which permits remote wireless communication with the controlling and monitoring electronics 43 to be ensured. The portable programming module 46 will ensure the operations of the keyboard and of the display of the electronics 43. Thus, an operator will be able to intervene in the operation of the apparatuses 40, by modifying the operational input commands directly from sites where the spraying apparatuses 40 are situated.

Advantageously, the system according to the invention will comprise means for regulating the supply from the pumps supplying the gaseous stream for the vaporising means of the apparatuses, and means for regulating the supply of fluid from the supply pumps for the flow accelerator means at the outlet of the apparatuses. The means for regulating the supply from the pumps may, for example, comprise respective solenoids, the opening and closing of which are controlled according to a predetermined frequency and by modifying the cyclical ratio.

Advantageously, also, the system according to the invention will comprise means for monitoring the level of liquid in the container of the apparatuses 40, according to any known means, for example an electric level gauge 41B, in order to stop the operation of the apparatuses, the liquid of which has been totally sprayed, and/or to carry out, manually or automatically, refilling of the containers with liquid, and/or simply to emit a warning signal.

Advantageously, also, the system according to the invention will comprise means for heating the liquid to be sprayed, for example by means of Peltier effect modules, situated below the container of the apparatuses 40. The system will equally comprise temperature sensors 41C for the liquid, in order to monitor and to control the operation of the Peltier effect modules relative to a temperature input command for the liquid. The system according to the invention will advantageously comprise one or more base plates, each of which permits at least one apparatus according to the invention to be supported and maintained, a base plate to which will be connected the heating means as well as one or more temperature sensors 41C.

Advantageously, also, the system according to the invention will comprise sensors 41D for the ambient temperature, and sensors 41E which permit measurement of the hygrometry.

The sensors 41A to 41E will be connected to the controlling and monitoring electronics 43, in order to permit, advantageously, an automatic operation of the system according to the invention relative to the measurements transmitted by these sensors.

The above-described system according to the invention is particularly suitable for the controlled diffusion of scents into the atmosphere, which scents may be different according to the apparatuses and the places in which these apparatuses are situated.

What is claimed is:

1. Apparatus which permits a liquid to be sprayed into the atmosphere, comprising:

a container (1), which is intended to contain said liquid (2) and has at least one outlet (3) for the liquid to be expelled from said container, said outlet being situated above said liquid, means (4) for generating a gaseous stream to expel said liquid from said container, means (5) for vaporising said liquid in said gaseous stream, and means (6) for spraying the vaporised liquid, comprising a column which is provided with baffles and is situated downstream of the vaporising means, wherein said vaporising means (5) and said spraying means (6) are integral with a body (7) capable of being engaged and maintained in a detachable manner in said outlet of the container (1), said body (7) including a duct (8) for expelling the liquid from the container, and wherein said column with baffles comprises a plurality of inclined walls (9) which form baffles on which said vaporised liquid comes to lodge, and in that said inclined walls form an angle ($\alpha$), greater than 90°, with a longitudinal flow direction (10) of the stream, so as to avoid a reverse flow of said stream.

2. Apparatus according to claim 1, characterised in that said vaporising means comprise a venturi (5).

3. Apparatus according to claim 1, wherein said inclined walls (9) each include a hole (11) for the passage of the stream, the respective holes of two successive walls (9) being offset.

4. Apparatus according to claim 3, wherein said hole (11) assumes the form of a venturi.

5. Apparatus according to claim 1, wherein two successive said inclined walls (9) are symmetrical relative to a plane (12) which is perpendicular to the longitudinal flow direction (10) of the stream.

6. Apparatus according to claim 1, wherein said means (4) for generating a gaseous stream to expel said liquid from said container comprise a flow accelerator (13) situated downstream of said spraying means (6).

7. Apparatus according to claim 6, wherein said flow accelerator comprises a fluid flow, which envelops said gaseous stream and the sprayed liquid downstream of the spraying means (6).

8. Apparatus according to claim 6, wherein said flow accelerator comprises a fluid flow conveyed in an axial manner into a venturi-type duct, which includes a tapering part followed by a cylindrical part, said gaseous stream and the sprayed liquid being introduced laterally into said cylindrical part of said venturi-type duct.

9. System which permits the spraying of a liquid into the atmosphere to be controlled, said system comprising:

one apparatus (40), which permits a liquid to be sprayed into the atmosphere according to claim 1, one gas sensor (41A), which permits measurement of the concentration of the liquid sprayed into the atmosphere, and means (42) for controlling the operation of said apparatus in dependence on at least one predetermined input command and on said measurement provided by said gas sensor.

10. An apparatus for spraying liquid into the atmosphere, the apparatus comprising:

a container adapted to contain liquid;

a pump generating a gaseous stream that expels liquid from said container; and a body detachably mounted on said container, said body comprising a generally tubular column with a vaporizer adjacent to said container that vaporizes liquid in the gaseous stream, and a sprayer duct with plural baffles stacked above said vaporizer, said baffles being stacked within said column and arranged so that the vaporized liquid ascends sequentially through said plural baffles and condensed liquid descends sequentially through said plural baffles.

11. The apparatus of claim 10, wherein said plural baffles comprise a plurality of inclined walls that form an angle of greater than 90° with a longitudinal axis of said tubular column.

12. The apparatus of claim 11, wherein said walls are separable and further comprising a plate between two of said walls for adjusting a distance between said walls.

13. The apparatus of claim 10, wherein said plural baffles are generally triangular with an apex and a base at opposite interior surfaces of said column.

14. The apparatus of claim 13, further comprising a hole adjacent to each said apex, and wherein said holes are arranged helically in said column.

15. The apparatus of claim 10, wherein said body comprises two tubular pieces, one of said two pieces being detachably mounted to said container and the other of said two pieces being detachably joined to said one piece, said other piece comprising said vaporizer and said sprayer duct.

16. The apparatus of claim 10, wherein said baffles are funnel-shaped.

* * * * *